US012623075B2

(12) United States Patent
Duijsens et al.

(10) Patent No.: US 12,623,075 B2
(45) Date of Patent: May 12, 2026

(54) CARDIAC DEVICE ADAPTER

(71) Applicant: Medtronic, Inc., Minneapolis, MN (US)

(72) Inventors: Victor Peter Jozef Duijsens, Grevenbicht (NL); Niels Martinus Josef van der Knaap, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 469 days.

(21) Appl. No.: 18/099,345

(22) Filed: Jan. 20, 2023

(65) Prior Publication Data

US 2023/0241383 A1 Aug. 3, 2023

Related U.S. Application Data

(60) Provisional application No. 63/305,574, filed on Feb. 1, 2022.

(51) Int. Cl.
*A61N 1/36* (2006.01)
*A61B 5/02* (2006.01)

(52) U.S. Cl.
CPC . *A61N 1/36* (2013.01); *A61B 5/02* (2013.01)

(58) Field of Classification Search
CPC .......... A61N 1/36; A61N 1/3752; A61B 5/02; A61B 5/287
See application file for complete search history.

(56) References Cited

U.S. PATENT DOCUMENTS

| | | | | |
|---|---|---|---|---|
| 5,070,605 A | * | 12/1991 | Daglow ............... | A61N 1/3752 439/933 |
| 5,679,026 A | * | 10/1997 | Fain ..................... | A61N 1/3752 439/651 |
| 8,140,163 B1 | * | 3/2012 | Daglow ............... | H01R 13/193 607/36 |
| 8,593,816 B2 | * | 11/2013 | Iyer ........................ | H01R 43/20 361/728 |
| 2004/0034392 A1 | * | 2/2004 | Spadgenske ......... | A61N 1/3752 607/37 |
| 2015/0133983 A1 | | 5/2015 | Loreth | |

(Continued)

FOREIGN PATENT DOCUMENTS

WO 00/11762 3/2000

OTHER PUBLICATIONS

International Search Report and Written Opinion for PCT/IB2023/050546 dated Mar. 21, 2023 (12 pages).

*Primary Examiner* — Catherine M Voorhees
(74) *Attorney, Agent, or Firm* — Mueting Raasch Group

(57) ABSTRACT

An adapter device that includes an adapter body having a first end and a second end. A connection interface is coupled to the first end, has a connection direction, and is configured to couple to a cardiac device. A receiving interface is disposed at the second end and has a receiving direction. The receiving interface includes a first receiving port that is in electrical communication with the connection interface and is configured to receive a first connector pin. A sealing member is configured to be sealably disposed over the receiving interface and configured to receive and frictionally engage at least a portion of the adapter body. In some embodiments, the connection direction and the receiving direction are the same. In some embodiments, the connection direction and the receiving direction are opposite.

16 Claims, 5 Drawing Sheets

(56)　　　　References Cited

U.S. PATENT DOCUMENTS

| | | | | | |
|---|---|---|---|---|---|
| 2020/0338355 | A1* | 10/2020 | Deininger | .......... | H01R 13/5224 |
| 2020/0353265 | A1* | 11/2020 | Ghosh | .................... | A61B 5/349 |
| 2022/0310329 | A1* | 9/2022 | McCurry | ................. | H01G 9/26 |
| 2022/0362559 | A1* | 11/2022 | Deininger | ............ | H01R 13/521 |

* cited by examiner

CARDIAC DEVICE ADAPTER

CROSS-REFERENCE TO RELATED APPLICATION

This application claims the benefit of U.S. Provisional Patent Application No. 63/305,574, filed Feb. 1, 2022, which is incorporated herein by reference in its entirety.

TECHNICAL FIELD

This disclosure generally relates to cardiac therapy. More particularly, the present disclosure relates to a lead to cardiac device adapter and methods of use thereof.

SUMMARY

The techniques of this disclosure generally relate to an adapter device and methods of use thereof.

This disclosure describes, in one aspect, an adapter device. The adapter device includes an adapter body with a first end and a second end, a connection interface, a receiving interface, and a sealing member. The connection interface is coupled to the first end, is configured to couple to a cardiac device, and has a connection direction. The receiving interface is disposed at the second end and has a receiving direction. The receiving interface includes a receiving port that is in electrical communication with the connection interface and is configured to receive a first connector pin. The sealing member is sealably disposed over the receiving interface and configured to receive and frictionally engage at least a portion of the adapter body.

In some embodiments, the receiving interface further includes a second receiving port that is configured to receive a second connector pin. The second receiving port is in electrical communication with the connection interface.

In some embodiments, the first receiving port is no greater than 15 mm in length.

In some embodiments, the first receiving port has a press fit connection. In some embodiments, a first securing mechanism is configured to fasten the first connector pin in the first receiving port. In some embodiments, the first securing mechanism includes a hook, a radial spring, a set screw, a curved receiving port, an angled receiving port, or an indented receiving port.

In some embodiments, the adapter device is no greater than 50 mm in length.

In some embodiments, the adapter device is no greater than 20 mm in height.

In some embodiments, the adapter device in no greater than 6 mm in width.

In some embodiments, the connection interface includes a pin electrical port and a ring electrical port arranged coaxially. In some embodiments, the connection interface is an IS-1 or an IS-4 interface.

In some embodiments, the connection direction and the receiving direction are the same.

In some embodiments, the connection direction and the receiving direction are opposite.

In another aspect, this disclosure describes a method of using a therapy device. The method includes inserting a first connector pin into a first receiving port of a receiving interface on a second end of an adapter device, including inserting the first connector pin through a sealing member of the adapter device. The method further includes coupling the sealing member to the adapter device. The method further includes coupling a first end of an adapter device to an implantable cardiac device. The method further includes applying a cardiac therapy from the implantable cardiac device for a period of time.

In some embodiments, the method further includes inserting a second connector pin into the second receiving port though the through a sealing member of the adapter.

In some embodiments, the method further includes implanting the therapy device in a subject.

In some embodiments, the method further includes coupling the therapy device to an outside surface of a body of a subject.

In some embodiments, the method further includes securing the sealing member to the adapter device using a suture wire.

In some embodiments, the method further includes using a suture wire to secure the sealing member to the adapter device.

In some embodiments, the first end of the adapter device comprises an IS-1 or IS-4 configuration.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The suffixes "a," "b," "c," and so on, may be used with a particular element number throughout this description and the figures to denote multiple parts/features having the same part/element name. The element number alone, without a suffix, is used herein to refer generally to one or more of the parts/elements having a suffix. In some instances, the parts/features denoted with a suffix may be substantially identical to, or mirror images of, one another. However, in some instances the parts/features denoted with a suffix may have differing configurations. The present description will govern.

Figure 1A:
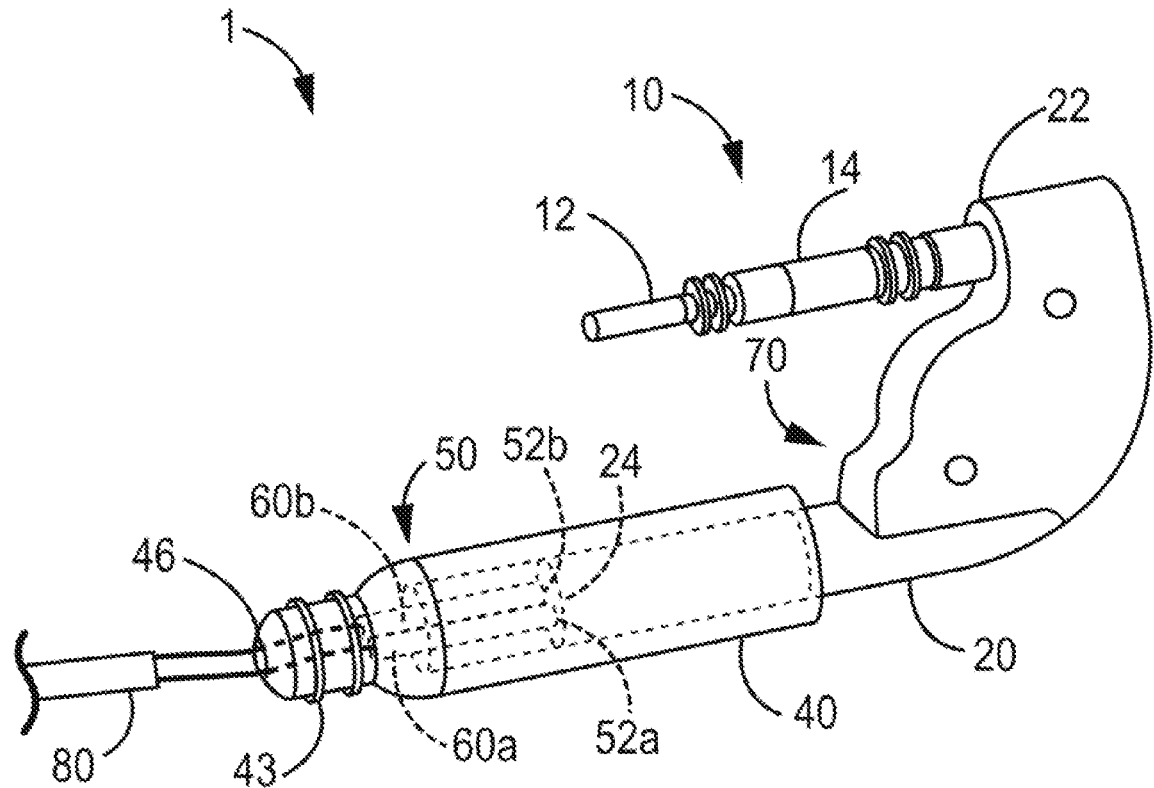
FIG. 1A depicts a view of an example adapter device consistent with the technology disclosed herein.
Figure 1B:
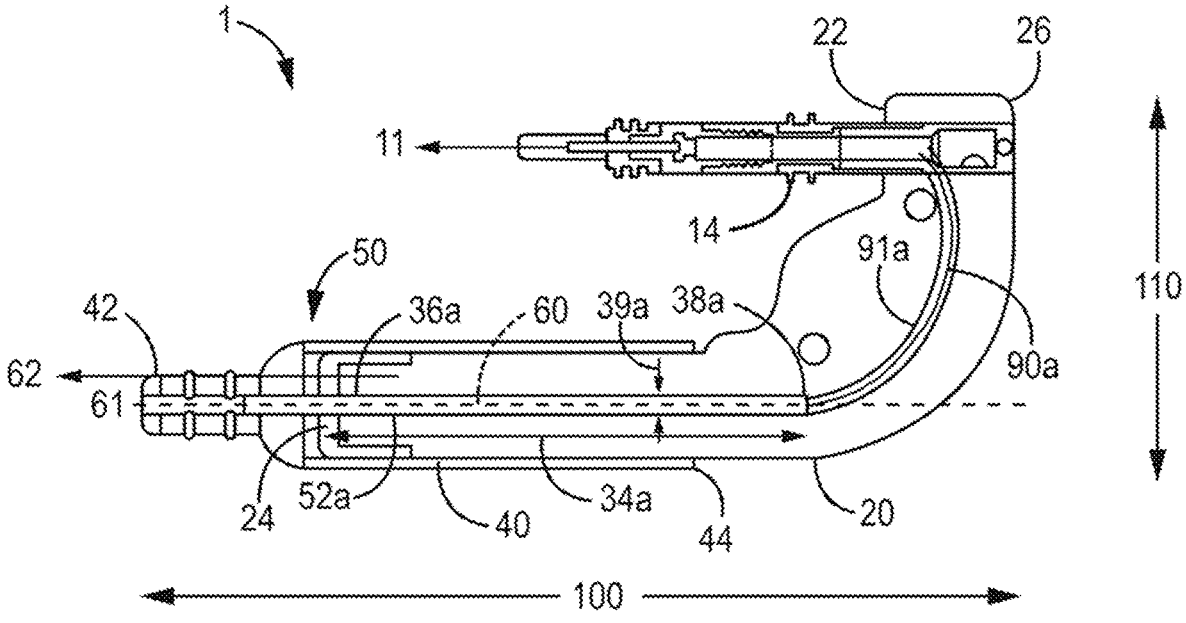
FIG. 1B depicts a cross sectional facing view of the example adapter device of FIG. 1A.

FIG. 1A and FIG. 1B depict a first view and a cross sectional view, respectively, of an example adapter device 1. The adapter device 1 is generally configured to electrically couple a cardiac device to one or more leads. In some embodiments, the cardiac device is a pacemaker. In some embodiments, the pacemaker is a temporary and/or implantable pacemaker. Furthermore, in some embodiments, the adapter device 1 is configured to allow for ambulatory pacing. In some embodiments, the adapter device 1 is configured to be implantable within a subject. In some embodiments, the adapter device 1 is configured to be coupled to the outside surface of the body of a subject.

The adapter device 1 includes an adapter body 20 that has a first end 22 and a second end 24. A connection interface 10 is coupled to the first end 22 of the adapter body 20. A receiving interface 50 is disposed at the second end 24 of the adapter body 20. A sealing member 40 is configured to be sealably disposed over the receiving interface 50 and a portion of the adapter body 20.

The adapter body 20 is generally configured to provide electrical communication between the connection interface 10 and the receiving interface 50. The adapter body 20 generally includes at least two conductors 90 (for example, 90*a* in FIG. 1B). As used herein, the term "conductor" refers to any material that is electrically conductive. The at least two conductors 90 may include any pair of suitable electrical conductors, such as coaxial conductors or side-by-side conductors. Examples of side-by-side conductors include "lamp cord" or "zip-cord" conductors as known in the art. In an exemplary embodiment depicted in FIG. 1B, the adapter body 20 has a pair of side-by-side conductors 90. The adapter body 20 has a first conductor 90*a* and a second conductor (not visible in the figures) that is disposed proximal to the first conductor 90*a*, in another possible configuration, the first conductor 90*a* may be helically wound around the second conductor. In some embodiments, the adapter body 20 may include more than two conductors, for example, three conductors, four conductors, five conductors, six conductors, seven conductors, or eight conductors.

In some embodiments, the adapter body 20 includes one or more insulative tubes and/or insulative coatings 91. In some embodiments, each conductor 90 may be independently coated with an insulative coating 91 and/or disposed within an insulative tube 91. The insulative coatings and/or tube 91 is generally configured to insulate the conductors 90 from each other and from the external environment outside the adapter body 20. In some embodiments, each conductor 90 may be independently coated with an insulative material 91. In some embodiments, each conductor 90 may be independently coated in an insulative material or disposed within an insulative tubing 91. Examples of insulative tube materials include polyethylene, silastic, neoprene, polypropylene, and polyurethane. Additionally, any insulative tube may be a heat shrink tube. A heat shrink tube is a tube that has a decrease in its internal diameter upon applying heat. Heat shrink tubes may be made of polytetrafloroethelene (PTFE), silicone, polyvinylidene fluoride, polyolefin, or fluorinated ethylene propylene. Insulative coatings include polyoxymethylene UV-cured adhesives; parylene, urethane, poly ether ketone (PEEK), and polyimide. In some embodiments, the insulative coating and/or the insulative tube 91 may be made of a biocompatible material (examples of biocompatible materials are described later). In some embodiments, the adapter body 20 serves as the insulative tube.

Returning to FIGS. 1A and 1B, the outer surface of adapter body 20 may be any biocompatible material. Exemplary biocompatible material include polyurethane; silicone; fluoropolymers such as tetrafluroethylene (ETFE), polytetrafluroethylene (PTFE); expanded PTFE such as porous ePTFE and nonporous ePTFE; stainless steel; titanium; titanium alloys; cobalt-chromium alloys; silicone; ceramic; and combinations thereof.

The connection interface 10 is generally configured to electrically couple to a cardiac device, such as an implantable pacemaker. As such, the connection interface 10 has a connection direction 11 (FIG. 1B). The connection direction 11 is defined as the direction the connection interface is facing to engage with the cardiac device. The connection interface 10 is in electrical communication with the two or more conductors 90 of the adapter body 20. The connection interface 10 may have a coaxial or side-by-side configuration. An example of a coaxial configuration is depicted in FIG. 1A and FIG. 1B. Specifically, the coaxial configuration includes a pin electrical port 12 and a ring electrical port 14. The pin electrical port 12 is in electrical communication with the first conductor 90*a*. Although not visible in FIG. 1B, the ring electrical port 14 is in electrical communication with the second conductor. An example of a coaxial connection interface 10 configuration is an IS-1 configuration known in the art. Another example of a coaxial connection interface 10 configuration is an IS-4 configuration known in the art.

The connection interface 10 is coupled to the first end 22 of the adapter body 20. In some embodiments, the connection interface 10 is coupled to the adapter body 20 using approaches known in the art. For example, the connection interface 10 can be coupled to the adapter body 20 using adhesive bonding; crimps or swages; fasteners such as screws, rivets, bolts, and the like; and combinations thereof. In some embodiments, the connection interface 10 may be integral with the adapter body 20 such as through welding, soldering, molding, or combinations thereof.

The receiving interface 50 is generally configured to provide electrical communication between a lead 80 and the connection interface 10. In some embodiments, the receiving interface 50 is configured to provide electrical communication between two or more leads and the connection interface 10. The lead 80 may be any temporary or permanent lead that is in electrical communication with the heart tissue of a subject. One or more connector pins 60 generally extend from each lead 80 (e.g., first connector pin 60*a* and second connector pin 60*b* as depicted in FIG. 1A). Generally, each connector pin 60 is in electrical communication with the lead 80 from which it extends. Electrical communication between the lead 80 and the connection interface 10 is accomplished through electrical communication of the connector pins 60 with the receiving interface 50. Electrical communication between the lead 80 and the connection interface 10 is accomplished through physical connection between each connector pins 60 and a corresponding receiving interface 50. The receiving interface 50 is also generally configured to secure the connector pins 60 within the adapter body 20. The receiving interface 50 is disposed at the second end 24 of the adapter body 20.

The receiving interface 50 includes one or more receiving ports 52 (e.g., a first receiving port 52*a* and a second receiving port 52*b* as depicted in FIG. 1A). Each receiving port 52 is generally configured to be in electrical communication with the connection interface 10. Each receiving port 52 has a first end 36 and a second end 38. For example, the first receiving port 52*a* has a first end 36*a* and a second end 38*a* (FIG. 1B). Although not visible in FIG. 1B, the second receiving port 52*b* has a first end and a second end. Each receiving port 52 is also generally configured to receive at least a portion of a connector pin 60 through the first end 36 of the receiving port 52 parallel to the receiving interface axis 61. For example, the first receiving port 52*a* is configured to receive at least a portion of the first connector pin 60*a* through the first end 36*a* of the first receiving port 52*a* parallel to the receiving interface axis 61. Additionally, the second receiving port 52*b* is configured to receive at least a portion of the second connector pin 60*b* through the first end 36*b* of the second receiving port 52*b* parallel to the receiving interface axis 61. In some embodiments, the connection interface 10 may include additional receiving ports. All additional receiving ports are generally configured to be in electrical communication with the connection interface 10. All additional receiving ports 52 are generally configured to receive at least a portion of a connector pin 60 through the first end of the receiving port along the receiving interface axis 61.

The receiving interface 50 has a receiving direction 62. The receiving direction 62 is defined as the direction the receiving interface 50 is facing to receive the one or more connector pins 60 through the one or more receiving ports 52. In particular, the receiving direction 62 extends outward from the receiving interface 50, parallel to the receiving interface axis 61.

Generally, each lead 80 includes one or more connector pins 60, each connector pin independently electrically coupled to an electrode. Commonly, the connector pins 60 are break-away pins coupled to a thorax needle. The ends of the connector pins 60 are exposed by breaking the thorax needle off the lead 80.

In some embodiments, the lead 80 is a heart wire. Heart wires are commonly used for temporary post cardiac surgery monitoring. A heart wire features one or more electrodes that are placed into the myocardium of subject and connector end. The connector end features a thorax needle and one or more break-away connector pins 60. In common practice, the connector end is led from the inside of the thorax to the outside body of the subject. The ends of connector pins 60 are then exposed by breaking the thorax needle away from the heart wire. Commonly, the connector pins 60 are connected to an external pacing device. However, heart wires used in this manner do not allow for the subject to be ambulatory. Advantageously, adapter device 1 may allow for heart wires to be connected with a temporary ambulatory pacing device.

A lead 80 may be classified by the number of connector pins 60 it has. For example, a lead 80 with one connector pin 60 is a monopolar lead. A lead 80 with two connector pins 60 is a bipolar lead.

In some embodiments, each receiving port 52 is configured to receive a connector pin 60 from a monopolar lead. In some embodiments, each receiving port 52 is configured to receive a connector pin 60 from bipolar lead. In some embodiments, as depicted in FIG. 1A, the first connector pin 60a and the second connector pin 60b are from the same bipolar lead 80. In other embodiments, the first connector pin 60a and the second connector pin 60b are from different bipolar leads. In other embodiments, the first connector pin 60a and the second connector pin 60b are from different monopolar leads. In some embodiments in which the receiving interface 50 has four receiving ports 52, the receiving ports 52 are configured to receive four connector pins 60 from two bipolar leads 80. In some embodiments in which the receiving interface 50 has four receiving ports 52, the receiving ports 52 are configured to receive four connector pins 60 from four monopolar leads 80. In some embodiments in which the receiving interface 50 has four receiving ports 52, the receiving ports 52 are configured to receive two connector pins 60 from two monopolar leads 80 and two connector pins 60 from one bipolar lead 80. The number of connector pins 60 the receiving interface 50 can accept is dependent on the configuration of the connection interface 10. For example, an IS-1 connection interface 10 configuration generally requires two receiving ports 52 that can receive one connector pin 60 each. Additionally, an IS-4 connection interface 10 configuration generally requires four receiving ports 52 that can receive one connector pin 60 each.

Each receiving port 52 has an axial length 34. Generally, the axial length 34 is configured to accommodate at least a portion of a connector pin 60. The axial length 34 is defined by the axial distance from the first end 36 to the second end 38 of the receiving port 52. For example, in FIG. 1B, the first receiving port 52a has an axial length 34a defined by the distance from the first end 36a of the receiving port 52a to the second end 38a of the receiving port 52a. Although not visible in FIG. 1B, the second receiving port 52b has an axial length 34b defined by the distance from the first end 36b of the receiving port 52b to the second end 38b of the receiving port 52b. In some embodiments, the axial length 34 of first receiving port 52a and second receiving port 52b are the same. In some embodiments, the axial length 34 of first receiving port 52a and second receiving port 52b are different. In some embodiments, where there are three or more receiving ports, all the axial lengths 34 may be the same. In some embodiments where there are three or more receiving ports, all the axial lengths 34 may be different. In some embodiments where there are three or more receiving ports, at least two of the axial lengths 34 may be the same.

Connector pins 60 may vary in length depending on the lead, the subject, and/or the application. In some embodiments, the axial length 34 of the receiving port 52 is no greater than 16 mm, no greater than 14 mm, no greater than 12 mm, no greater than 10 mm, no greater than 8 mm, no greater than 6 mm, or no greater than 4 mm. In some embodiments, the axial length 34 of the receiving port 52 is greater than 4 mm, greater than 6 mm, greater than 8 mm, greater than 10 mm, greater than 12 mm, or greater than 14 mm. In some embodiments, the axial length 34 is 4 mm to 16 cm, 4 mm to 14 mm, 4 mm to 12 mm, 4 mm to 10 mm, 4 mm to 8 mm, or 4 mm to 6 mm. In some embodiments, the axial length 34 of the receiving port 52 is 6 mm to 16 cm, 6 mm to 14 mm, 6 mm to 12 mm, 6 mm to 10 mm, or 6 mm to 8 mm. In some embodiments, the axial length 34 of the receiving port 52 is 8 mm to 16 cm, 8 mm to 14 mm, 8 mm to 12 mm, or 8 mm to 10 mm. In some embodiments, the axial length 34 of the receiving port 52 is 10 mm to 16 cm, 10 mm to 14 mm, or 10 mm to 12 mm. In some embodiments, the axial length 34 is 12 mm to 16 cm or 12 mm to 14 mm. In some embodiments, the axial length 34 of the receiving port 52 34 is 14 mm to 16 cm. In some embodiments the axial length 34 is 15 mm.

Each receiving port 52 has a diameter 39. For example, the first receiving port 52a has a diameter 39a. Although not visible in FIG. 1B, the second receiving port 52b has a diameter of 39b. The diameter 39 is generally configured to accommodate at least a portion of a connector pin 60. Connector pins 60 may have a variety of diameters depending on the lead, the subject, and/or the application. For example, the bipolar coaxial temporary pacing lead model 6495 (Medtronic, Inc. based in Fridley, MN) includes two connector pins 60 each having a diameter of 0.85 mm. Other connector pins may have a diameter greater than or less than 0.85 mm.

In some embodiments, the diameter 39 of the receiving port 52 is no greater than 1.4 mm, no greater than 1.2 mm, no greater than 1.0 mm, no greater than 0.8 mm, or no greater than 0.6 mm. In some embodiments, the diameter 39 of the receiving port 52 is greater than 0.6 mm, greater than 0.8 mm, greater than 1.0 mm, or greater than 1.2 mm. In some embodiments, the diameter 39 of the receiving port 52 is 0.6 mm to 1.4 mm, 0.6 mm to 1.2 mm, 0.6 mm to 1.0 mm, or 0.6 mm to 0.8 mm. In some embodiments, the diameter 39 of the receiving port 52 is 0.8 mm to 1.4 mm, 0.8 mm to 1.2 mm, or 0.8 mm to 1.0 mm. In some embodiments, the diameter 39 of the receiving port 52 is 1.0 mm to 1.4 mm or 1.0 mm to 1.2 mm. In some embodiments, the diameter 39 is 1.2 mm to 1.4 mm. In some embodiments, the diameter 39 is constant along the axial length 34 of the receiving port 52. In some embodiments, the diameter 39 is tapered along the axial length 34 of the receiving port 52 (discussed in further detail below). In some embodiments where there are two or more receiving ports 52, each diameter 39 may be different. In some embodiments where there are two or more receiving ports 52, each diameter 39 may be the same. In some embodiments where there are three or more receiving ports 52, two or more diameters 39 may be the same and one diameter 39 is different. In some embodiments, a receiving port 52 has a diameter 39 configured to receive connector pins 60 that have different diameters. For example, a receiving port 52 may have a diameter 39 that can receive a connector pin that has a 0.85 mm diameter and can receive a connector pin 60 that has a diameter that is greater than or less than 0.85 mm. A receiving port 52 that has a diameter 39 configured to receive connector pins 60 that have a variety of diameters may advantageously allow for connector pins 60 from different leads 80 to be electrically coupled to the receiving interface 50.

Electrical communication between each receiving port 52 and the connection interface 10 is established though the conductors 90 of the adapter body 20. For example, as depicted in FIG. 1B, the first receiving port 52*a* is in electrical communication with the first conductor 90*a*. Although not visible in FIG. 1B, the second receiving port 52*b* is in electrical communication with the second conductor.

In some embodiments, each receiving port 52 may include a securing mechanism. The securing mechanism is generally configured to maintain electrical communication between the connector pin 60 and the receiving interface 50. The securing mechanism is generally configured to prevent electrical communication disruption between the connector pin 60 and the receiving interface 50. The securing mechanism is generally configured to maintain physical engagement of the connector pin 60 within the receiving port 52. The securing mechanism is generally configured to prevent the connector pin 60 from dislodging from the receiving port. In some embodiments the securing mechanism is configured to advantageously allow the receiving port 52 to accommodate connector pins 60 with a variety of radial diameters. In some embodiments, each connector pin 60 is inserted into a receiving port 52 along the receiving interface axis 61 to establish electrical communication through the securing mechanism.

The securing mechanism may have a variety of configurations known in the art. In some embodiments, the securing mechanism is a press fit configuration. In the press fit configuration, the connector pin 60 inserted in in the receiving port 52 along the receiving interface axis 61 and is frictionally engaged by the receiving port 52, thus establishing physical engagement and electrical connection between the connection interface 10 and the connector pin 60. Advantageously, a press fit configuration allows for the securing of the connector pin within the receiving port 52 without the need for additional components such as set screws. The press fit connection can be formed through a variety of approaches. For example, in some embodiments, securing mechanism has a radial spring configuration. The radial spring can extend radially inward from the port, which is configured to exert frictional force on the pin 60 in the radial direction. In some embodiments the press fit connection is formed through a curved port where the receiving 52 port is curved from the first end 36 to the second end 38 which causes frictional engagement of the connector pin 60 within the receiving port 52. In some embodiments, the receiving port 52 has an angle from the first end 36 to the second end 38 allowing for frictional engagement of the connector pin 60 within the receiving port 52. In some embodiments, the receiving port 52 may include one or more hooks that extend inwardly from the interior wall of the receiving port 52 to engage the connector pin 60. In some embodiments, the receiving port 52 may include indentations configured to engage corresponding ribs defined by the connector pin in a press fit configuration. Other securing mechanisms include glue, set screws, and the like. In some embodiments the securing mechanism does not include a set screw.

Returning to FIG. 1A and FIG. 1B, the sealing member 40 is generally configured to receive and frictionally engage at least a portion of the adapter body 20. The sealing member 40 is generally configured to prevent debris from contacting the receiving interface. The sealing member 40 is generally configured to prevent debris from entering the receiving ports. The sealing member is generally configured to provide a fluid tight connection between the adapter body 20 and the sealing member 40. The sealing member may be made of any biocompatible material that is elastic. Examples of biocompatible materials include, but are not limited to, polyurethane; silicone; fluoropolymers such as tetrafluroethylene (ETFE), polytetrafluroethylene (PTFE); expanded PTFE such as porous ePTFE and nonporous ePTFE; silicone; and combinations thereof. In some embodiments, the sealing member is made of silicone.

The sealing member 40 has a first end 42 and a second end 44. The first end 42 is generally configured to allow the one or more connector pins 60 to pass through the sealing body. In some embodiments, the first end 42 may include an opening 46. In some embodiments, the first end 42 is configured to be punctured by a puncturing device such as needle, to create an opening 46. In some embodiments, the one or more connector pins 60 is a break-away pin that is coupled to a thorax needle. The thorax needle is used as the puncturing device to puncture the first end 42 of the sealing member 40 creating an opening 46. The thorax needle and the one or more break-away connector pins 60 are pulled through the opening 46. The end of each connector pin is exposed after the thorax needle is removed, or broken off, the lead 80. The one or more connector pins 60 are then inserted into the one or more receiving ports 52 to establish electrical communication between each connector pin 60 and the receiving interface 50.

The second end 44 of the sealing member 40 is configured to receive at least a portion of the adapter body 20 towards the second end 24 of the adapter body 20. Following establishment of electrical communication between each connector pin 60 and the receiving interface 50 as described previously, the second end 44 of the sealing member 40 is pulled/pushed over the second end 24 of adapter body 20. The sealing member 40 is configured to create a frictional seal with the adapter body 20. In some embodiments, additional components may be used to enhance or aid in sealing the sealing member 40 to the adapter body 20. For example, in some embodiments, a suture wire or sutures may be used to seal the sealing member 40 to the adapter body 20. In some embodiments, the sealing member 40 includes one or more radial rims 43 configured to maintain the position of the sutures. In some embodiments, glue may be used to seal the sealing member 40 to the adapter body 20.

Figure 1C:
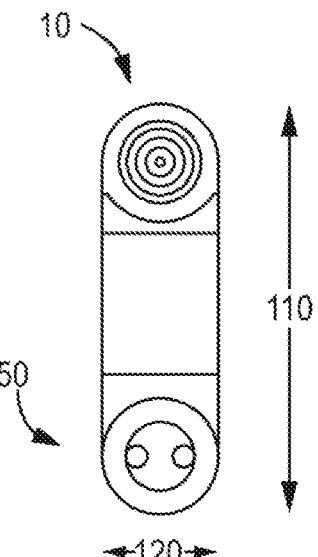
FIG. 1C depicts a second view of an example adapter device of FIG. 1A.

As depicted in FIGS. 1B and 1C, the adapter device 1 has an axial length 100, a height 110, and a width 120. Generally, the dimensions of the adapter device 1 are configured to allow the adapter device 1 to have a relatively small three-dimensional footprint in space. A small three-dimensional footprint may advantageously facilitate implantation into a subject.

The axial length 100 is defined as the distance from a first end of the adapter device 1 (which here is the first end 42 of the sealing member 40) to a second, opposite end 26 of the adapter device 1 parallel to the receiving interface axis 61. Generally, relatively short axial lengths are preferred. Relatively large axial lengths limit the use of the adapter device 1 as an implantable device. Although there is no particular lower limit, in practice the axial length 100 of the adapter device 1 may be greater than 20 mm, greater than 30 mm, greater than 40 mm, greater than 50 mm, or no greater than 60 mm. In some embodiments, the axial length 100 of the adapter device 1 may be no greater than 70 mm, no greater than 60 mm, no greater than 50 mm, no greater than 40 mm, no greater than 30 mm, or no greater than 20 mm. In some embodiments, the axial length 100 of the adapter device 1 is 20 mm to 70 mm, 20 mm to 60 mm, 20 mm to 50 mm, 20 mm to 40 mm, or 20 mm to 30 mm. In some embodiments, the axial length 100 of the adapter device 1 is 30 mm to 70 mm, 30 mm to 60 mm, 30 mm to 50 mm, or 30 mm to 40 mm. In some embodiments, the axial length 100 of the adapter device 1 is 40 mm to 70 mm, 40 mm to 60 mm, or 40 mm to 50 mm. In some embodiments, the axial length 100 of the adapter device 1 is 50 mm to 70 mm or 50 mm to 60 mm. In some embodiments, the axial length 100 of the adapter device 1 is 60 mm to 70 mm. In some embodiments the axial length 100 of the adapter device 1 is 40 mm to 50 mm. In some embodiments, the axial length 100 of the adapter device 1 is 48 mm.

As depicted in FIG. 1B and FIG. 1C, the height 110 is defined as the distance from one end of the adapter device 1 to another end of the adapter device 1 in a direction perpendicular to the axial length 100. Generally, smaller heights are preferred. Relatively large heights limit the use of the adapter device 1 as an implantable device. Although there is no particular lower limit, in practice the height 110 of the adapter device 1 may be greater than 12 mm, greater than 14 mm, greater than 16 mm, greater than 18 mm, or greater than 20 mm. In some embodiments, the height 110 of the adapter device 1 may be no greater than 22 mm, no greater than 20 mm, no greater than 18 mm, no greater than 16 mm, no greater than 14 mm, or no greater than 12 mm. In some embodiments, the height 110 of the adapter device 1 is 12 mm to 22 mm, 12 mm to 20 mm, 12 mm to 18 mm, 12 mm to 16 mm, or 12 mm to 14 mm. In some embodiments, the height 110 of the adapter device 1 is 14 mm to 22 mm, 14 mm to 20 mm, 14 mm to 18 mm, or 14 mm to 16 mm. In some embodiments, the height 110 of the adapter device 1 is 16 mm to 22 mm, 16 mm to 20 mm, or 16 mm to 18 mm. In some embodiments, the height 110 of the adapter device 1 is 18 mm to 22 mm or 18 mm to 20 mm. In some embodiments, the height 110 of the adapter device 1 is 20 mm to 22 mm. In some embodiments, the height 110 of the adapter device 1 is 16 mm to 18 mm. In some embodiments, the height 110 of the adapter device 1 is 18 mm to 20 mm. In some embodiments, the height 110 of the adapter device 1 is 18 mm.

As depicted in FIG. 1C, the width 120 is defined that the width of the adapter body 20 in a direction perpendicular to the height and the axial length. Generally, smaller widths are preferred. Relatively large widths limit the use of the adapter device 1 as an implantable device. Although there is no particular lower limit, in practice the width 120 of the adapter device 1 may be greater than 3 mm, greater than 4 mm, greater than 5 mm, or greater than 6 mm. In some embodiments, the width 120 of the adapter device 1 may be no greater than 7 mm, no greater than 6 mm, no greater than 5 mm, no greater than 4 mm, or no greater than 3 mm. In some embodiments, the width 120 of the adapter device 1 may be 3 mm to 7 mm, 3 mm to 6 mm, 3 mm to 5 mm, or 3 mm to 4 mm. In some embodiments, the width 120 of the adapter device 1 may be 4 mm to 7 mm, 4 mm to 6 mm, or 4 mm to 5 mm. In some embodiments, the width 120 of the adapter device 1 may be 5 mm to 7 mm or 5 mm to 6 mm. In some embodiments, the width 120 of the adapter device 1 may be 6 mm to 7 mm. In some embodiments, the width 120 of the adapter device 1 is 5 mm to 6 mm. In some embodiments, the width 120 of the adapter device 1 is 5.8 mm.

In some embodiments, as depicted in FIG. 1A, FIG. 1B, and FIG. 1C the connection direction 11 of the connection interface 10 is parallel to the receiving direction 62 of the receiving interface 50. In some embodiments, the connection direction 11 and the receiving direction 62 in the same direction (FIG. 1B). In this configuration, the adapter body 20 includes a cavity 70 configured to receive the cardiac device. An advantage of the connection direction 11 and the receiving direction 62 being the same, is a relatively reduced axial length 100 of the adapter device 1. An advantage of the connection direction 11 and the receiving direction 62 being the same, is a reduced axial length 100 when the adapter device 1 is coupled to the cardiac device. This configuration allows the assembly of the adapter device 1 and the cardiac device to be shorter than a configuration in which the length of the adapter device 1 is added to the length of the cardiac device (like in FIG. 2). Reducing the axial length 100 may advantageously facilitate implantation of the adapter device 1 within a subject. Reducing the axial length 100 may advantageously allow subject to be ambulatory post implantation. Additionally, shorter axial lengths may reduce discomfort related to the implanted adapter device 1 when the subject is ambulatory. Generally, the ability of the adapter device 1 to adjust to the motion of a subject in which it is implanted, is impacted by the axial length 100. The longer the axial length 100, the higher the likelihood that the adapter device causes discomfort for the subject when the subject is ambulatory. As such, an adapter device 1 with a relatively long axial length 100 may protrude from the implantation location, restricting the motion of a subject. In contrast, shorter axial lengths may facilitate a relatively wider range of motion without discomfort compared to relatively longer axial lengths.

Figure 2:
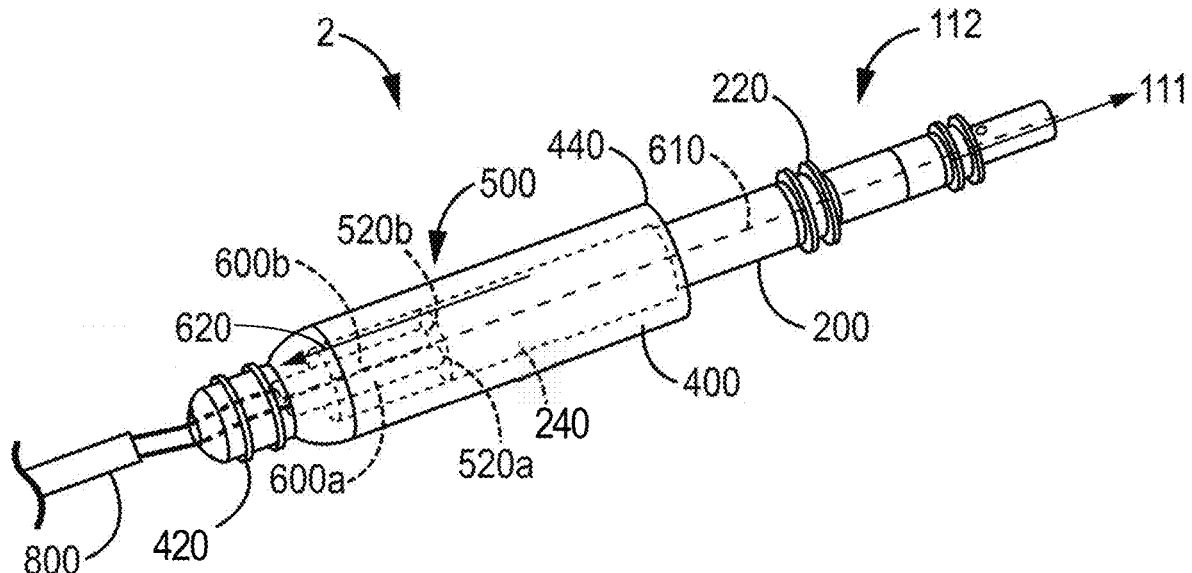
FIG. 2 depicts a schematic view of a cross sectional facing view of example adapter device consistent with the technology disclosed herein.

FIG. 2 is a schematic view of an adapter device 2 consistent with another embodiment of the present disclosure. The adapter device 2 is generally configured to electrically couple a cardiac device to one or more leads 800. In some embodiments, the cardiac device is a pacemaker. In some embodiments, the pacemaker is a temporary and/or implantable pacemaker. Furthermore, in some embodiments, the adapter device 2 is configured to allow for ambulatory pacing. In some embodiments, the adapter device 2 is configured to be implantable within a subject. In some embodiments, the adapter device 2 is configured to be coupled to the outside surface of the body of a subject.

The adapter device 2 includes an adapter body 200 that has a first end 220 and a second end 240. A connection interface 112 is coupled to the first end 220 of the adapter body 200. A receiving interface 500 is disposed at the second end 240 of the adapter body 200. A sealing member 400 is configured to be sealably disposed over the receiving interface 500 and a portion of the adapter body 200.

The adapter body 200 is generally configured to provide electrical communication between the connection interface 112 and the receiving interface 500. The adapter body 200 may have any configuration as described elsewhere in the present disclosure. The adapter body 200 may be made of any materials as described elsewhere in the present disclosure.

The connection interface 112 is generally configured to electrically couple to a cardiac device, such as an implantable pacemaker. As such, the connection interface 10 has a connection direction 111 (FIG. 2). The connection direction 111 is defined as the direction the connection interface is facing to engage with the cardiac device. The connection interface 112 is coupled to the second end 220 of the adapter body 200. The connection interface may have any configuration as described elsewhere in the present disclosure.

The receiving interface 500 is generally configured to provide electrical communication between a lead 800 and the connection interface 112. The receiving interface 500 is disposed at the second end 240 of the adapter body 200. The receiving interface 500 may have any configuration as discussed elsewhere in the present disclosure.

The receiving interface 500 includes one or more receiving ports 520 (e.g., a first receiving port 520a and a second receiving port 520b as depicted in FIG. 2). Each receiving port 520 is generally configured to be in electrical communication with the connection interface 112. Each receiving port 520 is configured to receive a connector pin 600 extending from a lead 800. Each receiving port may have any configuration as discussed elsewhere in the present application.

The receiving interface 500 has a receiving direction 620. The receiving direction 620 is defined as the direction the receiving interface 500 is facing to receive the one or more connector pins 600 through the one or more receiving ports 520. In particular, the receiving direction 620 is outward from the receiving interface 500, parallel to the axial direction/receiving to the receiving interface axis 610.

The sealing member 400 is generally configured to receive and frictionally engage at least a portion of the adapter body 200. The sealing member 400 has a first end 420 and a second end 440. The second end 440 of the sealing member 400 is configured to receive at least a portion of the adapter body 200 towards the second end 240 of the adapter body 200. The sealing member 400 may have any configuration as discussed elsewhere in the present application. The sealing member 400 may be made of any material as discussed elsewhere in the present application.

In contrast to adapter device 1 (FIG. 1A and FIG. 1B), the connection direction 111 and the receiving direction 620 of adapter device 2 are oriented in the opposite direction. In this configuration, the connection interface 112 and the receiving interface 500 are generally aligned. Additionally, in this configuration the adapter body 200 generally is cylindrical. An advantage of an opposite orientation of the connection direction 111 and the receiving direction 620, is the reduced complexity of the adapter device 2. The reduced complexity may simplify manufacturing. The reduced complexity may allow for reduced costs of production. Furthermore, the reduced complexity may allow for reduced consumer costs.

Figure 3:
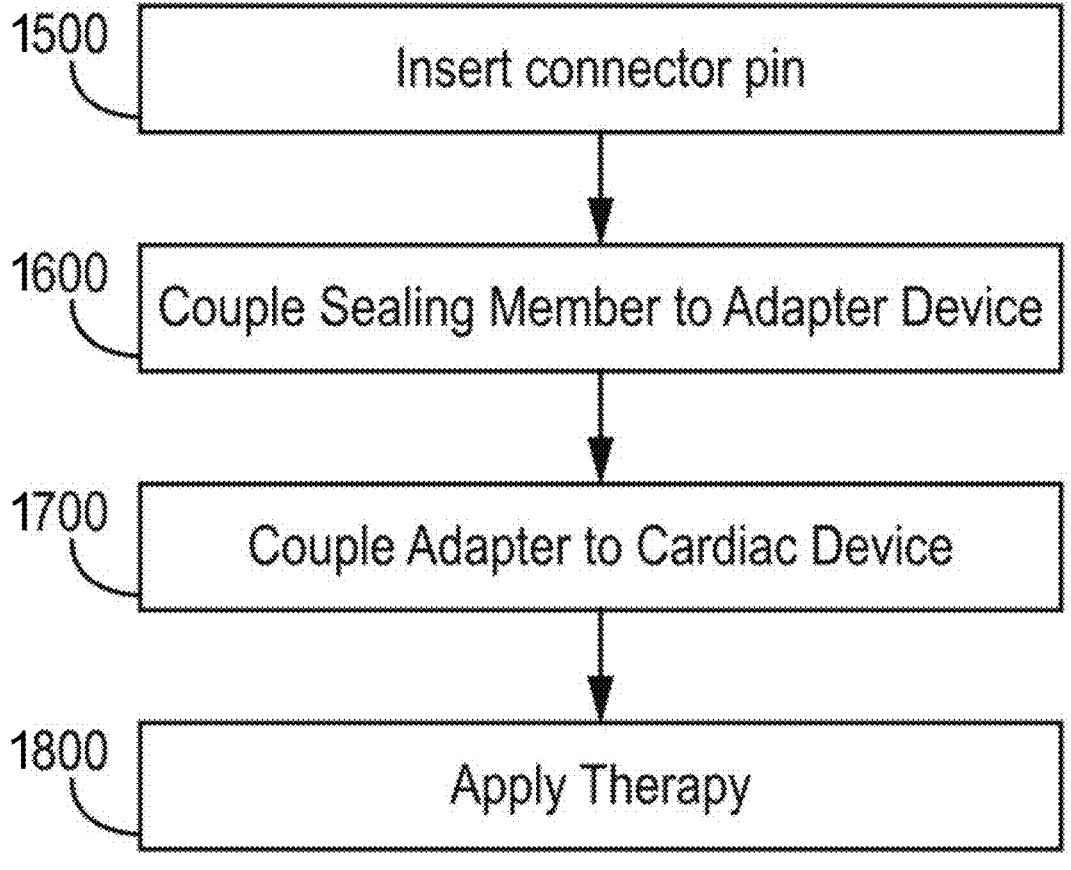
FIG. 3 depicts a flow diagram of a method of using an adapter device consistent with embodiments of the present disclosure.

FIG. 3 describes a method for using a therapy device consistent with the present disclosure. Generally, the method includes inserting one or more connector pins into a receiving port 1500, coupling a sealing member to an adapter device 1600, coupling the adapter device to a cardiac device 1700, and applying cardiac therapy 1800. In some embodiments, the adapter device is provided as previously described relative to FIG. 1A, FIG. 1B, FIG. 1C, and FIG. 2.

Inserting one or more connector pins into a receiving port 1500 includes inserting a first connector pin into a first receiving port of a receiving interface on a second end of an adapter device through a sealing member. In some embodiments, the sealing member is punctured. The puncture creates an opening through which the first connector pin may pass. In some embodiments, a needle is used to puncture the sealing member and create the opening. In some embodiments, the connector pin is a break-away connector pin that is coupled to a needle, such as a thorax needle. The thorax needle is used to puncture the sealing member creating an opening. The thorax needle and the coupled break-away connector pin is pulled through the opening.

Inserting the first connector pin into a first receiving port further includes establishing an electrical connection between the connector pin and the receiving interface. Establishing the electrical connection may be achieved by pushing the connector pin into the first receiving port. A securing mechanism establishes a physical connection between the connector pin and the receiving port. The securing mechanism also holds the connector pin within in the receiving port. The physical connection establishes electrical communication between the connector pin and the receiving interface. A variety of securing mechanisms may be used, such as those discussed elsewhere in the present application. In some embodiments, the securing mechanism is a press fit mechanism. In a press fit mechanism, the connector pin is pushed into the receiving port and is frictionally engaged by the receiving port. Example press fit securing mechanisms include radial spring configurations, curved receiving ports, angles receiving ports, receiving ports that include indents, receiving ports that include hooks, and combinations thereof. Other securing mechanism that may be used include, but are not limited to glue, set screws, and the like.

In some embodiments, where the first connector pin is a break-away connector pin coupled to a thorax needle, the end of the connector pin is first exposed by breaking off the thorax needle. The now exposed end of the connector pin is inserted into the first receiving port so that at least a portion of the connector pin is disposed within the receiving port. In some embodiments a second connector pin is inserted into a second receiving port in accordance with the method as previously described. In some embodiments, one or more additional connector pins are each inserted into a corresponding additional receiving port following the method as previously described.

Coupling a sealing member to an adapter device includes establishing a fluid tight seal around the receiving interface and at least a portion of the adapter device. In some embodiments, the sealing member is pulled/pushed over the second end of adapter device. In some embodiments, additional components may be used to enhance or aid in sealing the sealing member to the adapter device. For example, in some embodiments, a suture wire or sutures may be used to secure the sealing member to the adapter device. In some embodiments, glue may be used to secure the sealing member to the adapter device. In some embodiments, any open space inside the sealing member may be backfilled with glue, such as silicon glue.

Coupling the adapter device to a cardiac device 1700 includes coupling the first end of an adapter device to an implantable cardiac device includes establishing an electrical connection between the adapter device and the implantable cardiac device. The first end of the adapter device is inserted into a compatible receiver on the implantable cardiac device. In some embodiments, the first end of the adapter device has an IS-1 or IS-4 configuration. In some embodiments, the IS-1 or IS-4 configuration of the adapter device is inserted into the compatible receiver of an implantable cardiac device.

In some embodiments, the method further includes implanting the therapy device in a subject. Generally, a surgeon will implant the therapy device at an appropriate location within the body of a subject. The implantation procedure may include securing the therapy device to tissue and/or bone. The implantation procedure may occur after the adapter device is coupled to the implantable cardiac device. In some embodiments, the implantable cardiac device is a temporary ambulatory pacemaker. Implanting the therapy device may allow for the subject to be ambulatory during the application of the cardiac therapy.

In some embodiments, the method further includes coupling the therapy device to an outside surface of a body of a subject. The therapy device may be coupled to any suitable exterior body surface of a subject. Coupling the therapy device to the surface of the body of a subject may include securing the therapy device using methods known in the art such as using tap, sutures, glue, and the like. Coupling the therapy device to an exterior body surface of a subject may allow for the subject to be ambulatory during the application of the cardiac therapy.

Cardiac therapy is applied 1800 by the implantable pacing device through the adapter device for a period of time. In some embodiments, the cardiac therapy is cardiac pacing therapy. In some embodiments, the cardiac therapy is temporary. In some embodiments, the cardiac therapy is ambulatory pacing therapy. In some embodiments, the cardiac therapy may be for at least 5 days, at least 20 days, at least 50 days, or at least 90 days. In some embodiments, the cardiac pacing therapy may be for less than 180 days, less than 90 days, less than 50 days, or less than 20 days. In some embodiments, the cardiac therapy may be applied for 5 days to 20 days, 5 days to 50 days, 5 to 90 days, or 5 to 180 days. In some embodiments, the cardiac pacing therapy may be applied for 20 days to 50 days, 20 to 90 days, or 20 to 180 days. In some embodiments, the cardiac therapy may be applied for 50 days to 90 days or 50 days to 180 days. In some embodiments, the cardiac therapy may be applied for 90 days to 180 days. In some embodiments, the cardiac therapy may be applied for more than 180 days.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An adapter device comprising:
   an adapter body with a first end and a second end, a connection interface coupled to the first end and having a connection direction, wherein the connection interface is configured to couple to a cardiac device and the connection direction is defined as the direction the connection interface is facing to receive the cardiac device;
   a receiving interface disposed at the second end and having a receiving direction, wherein the connection direction and the receiving direction are the same, the receiving interface comprising:
   a first receiving port configured to receive a first connector pin, the first receiving port in electrical communication with the connection interface; and
   a sealing member configured to be sealably disposed over the receiving interface and configured to receive and frictionally engage at least a portion of the adapter body, wherein the receiving direction is defined as the direction the receiving interface is facing to receive the first connector pin.

2. The adapter device of claim 1, wherein the receiving interface further comprises a second receiving port configured to receive a second connector pin, the second receiving port in electrical communication with the connection interface.

3. The adapter device of claim 1, wherein the first receiving port is no greater than 15 mm in length.

4. The adapter device of claim 1, wherein the first receiving port has a press fit connection.

5. The adapter device of claim 1, wherein a first securing mechanism is configured to fasten the first connector pin in the first receiving port.

6. The adapter device of claim 5, wherein the first securing mechanism comprises a hook, a radial spring, a set screw, a curved receiving port, an angled receiving port, or an indented receiving port.

7. The adapter device of claim 1, wherein the adapter device is no greater than 50 mm in length.

8. The adapter device of claim 1, wherein the adapter device is no greater than 20 mm in height.

9. The adapter device of claim 1, wherein the adapter device is no greater than 6 mm in width.

10. The adapter device of claim 1, wherein the connection interface comprises a pin electrical port and a ring electrical port arranged coaxially.

11. The adapter device of claim 10, wherein the connection interface comprises an IS-1 or an IS-4 interface.

12. A method of using an implantable cardiac device, the method comprising:
   inserting a first connector pin into a first receiving port of a receiving interface on a second end of an adapter device, including inserting the first connector pin through a sealing member of the adapter device, wherein the receiving interface has a receiving direction that is defined as the direction the receiving interface is facing to receive the first connector pin;
   coupling the sealing member to the adapter device;
   coupling a first end of the adapter device to an implantable cardiac device, wherein the first end of the adapter device defines a connection interface having a connection direction, which is defined as the direction the connection interface is facing to receive the cardiac device, and wherein the receiving direction and the connection direction are the same;
   coupling the adapter device to an outside surface of a body of a subject; and
   applying a cardiac therapy from the implantable cardiac device for a period of time.

13. The method of claim 12, further comprising inserting a second connector pin into the second receiving port through the sealing member of the adapter.

14. The method of claim 12, further comprising coupling the implantable cardiac device to an outside surface of a body of a subject.

15. The method of claim 12, wherein the method further comprising securing the sealing member to the adapter device using a suture wire.

16. The method of claim 12, wherein the first end of the adapter device comprises an IS-1 or IS-4 configuration.

* * * * *